United States Patent [19]

Van Ooijen

[11] Patent Number: 5,380,939

[45] Date of Patent: Jan. 10, 1995

[54] RELEASABLY BOUND CARBOXYLIC ACIDS

[75] Inventor: Johannes A. C. Van Ooijen, Giessenburg, Netherlands

[73] Assignee: BP Chemicals Limited, London, England

[21] Appl. No.: 126,050

[22] Filed: Sep. 23, 1993

[30] Foreign Application Priority Data

Sep. 30, 1992 [GB] United Kingdom ............... 9220616
Oct. 14, 1992 [GB] United Kingdom ............... 9221528

[51] Int. Cl.$^6$ ...................... C07C 53/08; C07C 53/10
[52] U.S. Cl. ........................................................ 562/607
[58] Field of Search .......................................... 562/607

[56] References Cited

U.S. PATENT DOCUMENTS 3,985,904  10/1976  Bernotavicz ..................... 426/332

FOREIGN PATENT DOCUMENTS 3201940  9/1991  Japan .
1694568  11/1991  U.S.S.R. .

*Primary Examiner*—Jose G. De
*Assistant Examiner*—Joseph M. Conrad, III
*Attorney, Agent, or Firm*—Brooks Haidt Haffner & Delahunty

[57] ABSTRACT

This invention relates to a composition for and method of storing and using acetic acid or propionic acid, the composition comprising an alkali(ne earth) metal salt of acetic acid or propionic acid and an aliphatic carboxylic acid which has a pKa value lower than that of acetic acid or propionic acid respectively. When this composition is brought into contact with a solvent system capable of allowing ionisation of the salt and the aliphatic carboxylic acid, free acetic acid or propionic acid is released in situ. This method enables the free acids to be stored and released at the point of use thereby substantially reducing the risks of corrosion and unpleasant odors.

7 Claims, No Drawings

RELEASABLY BOUND CARBOXYLIC ACIDS

This invention relates to a method of storing and using acetic or propionic acid releasably bound on a support.

It is well known that acetic acid and propionic acids are relatively strong organic acids which are also corrosive. Yet these acids have a considerable number of uses, not least in the field of agriculture, e.g., for the protection of crops, preparation of silage and as a salmonella control agent. However, the storage and transportation of acetic acid and propionic acids is rather difficult due to their corrosivity and their pungent smell. Various methods have been tried to immobilize acetic and propionic acids but with inadequate success either because of the strong bond formed between these acids and the support thereby not being readily releasable at the point of use or because of a relatively weak bond whereby the acid evaporates from the support too readily and hence results in loss of the acid and risks polluting the environment surrounding the point of storage.

It has now been found that these problems can be mitigated by using an alkali(ne earth) metal propionate with another carboxylic acid of defined physical properties such that free acetic acid or propionic acid is released at the point of use.

Accordingly the present invention is a composition comprising an acetate or a propionate salt of an alkali(ne earth) metal and an aliphatic carboxylic acid which has a lower pKa value than that of acetic acid or propionic acid respectively.

A feature of the invention is that the alkali(ne earth) acetates or propionates when used in a medium capable of allowing dissociation of the salt of free carboxylic acids into anions and cations, e.g., in aqueous systems, also dissociates into the alkali(ne earth) metal ions and acetate or propionate ions and the aliphatic carboxylic acid in turn dissociates into the corresponding carboxylate ion and hydrogen ions. However, due to the relative differences in the pKa values, the aliphatic carboxylate ion combines with the alkali(ne earth) metal ion to form the alkali(ne earth) metal salt of the aliphatic carboxylic acid and releases acetic or propionic acid in situ.

The process works particularly efficiently if the alkali(ne earth) metal salt of the aliphatic carboxylic acid so formed is readily soluble in the solvent system used to generate the desired acetic or propionic acid. However, for practical reasons it may be preferable, though not essential, to form a substantially insoluble alkali(ne earth) metal salt in order to enable easy separation of the acetic or propionic acid solution from the insoluble salt by decantation or filtration immediately prior to use. Such an insoluble salt can be formed by the appropriate selection of reagents and/or solvents. It should be noted, however, that in the process of separating the acetic or propionic acid solution from the precipitate, some of the yield of available acetic or propionic acid may be lost due to occlusion on the precipitate.

Particularly suitable alkali(ne earth) metal salts for use in the compositions of the present invention are those of sodium, potassium, calcium and magnesium.

Propionic acid has a pKa value (i.e. dissociation constant) of about 4.87 in water at 25° C. Thus any aliphatic carboxylic acid which has a lower pKa value under comparable conditions would be suitable for admixing with the alkaline earth metal propionate.

Similarly, acetic acid has a pKa value (i.e. dissociation constant) of about 4.75 in water at 25° C. Thus any aliphatic carboxylic acid which has a lower pKa value under comparable conditions would be suitable for admixing with the alkaline earth metal acetate.

Such aliphatic carboxylic acids which have a pKa value lower than that of acetic or propionic acid may be mono-, di- or poly-carboxylic acids and may be saturated or unsaturated. Particularly suitable for this purpose are the di- and polycarboxylic acids, especially the unsaturated carboxylic acids due to their ability to form alkaline earth metal salts which have very low solubility in aqueous systems, e.g. water. Specific examples of the preferred aliphatic carboxylic acids include transfumaric acid (pKa 3.03 and 4.44), furoic acid (pKa 3.17), furan carboxylic acid (pKa 3.15) lactic acid (pKa 3.08), maleic acid (pKa 1.83), malic acid (pKa 3.40), oxalic acid (pKa 1.23), malonic acid (pKa 2.38), succinic acid (pKa 4.16), suberic acid (pKa 4.52), mesaconic acid (pKa 3.09 and 4.75), methyl malonic acid (pKa 3.07), methyl succinic acid (pKa 4.13), gallic acid (pKa 4.41), alpha-tartaric acid (pKa 2.98) and meso-tartaric acid (pKa 3.22).

For instance, if fumaric acid, which has a substantially low volatility, is intimately mixed with a calcium acetate or calcium propionate salt and stored as such the problems of odour and corrosivity are immediately alleviated. However, when the fumaric acid admixed with calcium acetate or calcium propionate is brought into contact with a suitable solvent, e.g. water, at the point of use and at room temperature, then a rapid exchange of ions takes place and the respective acetic or propionic acid is liberated immediately into the aqueous solution in situ leaving behind a substantially insoluble precipitate of calcium fumarate which can be readily removed either by decantation or filtration.

The filtrate containing the acetic or propionic acid in solution and some calcium fumarate can then be used as desired.

The above reaction can be represented as follows:

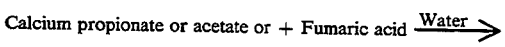

The alkali(ne earth) metal acetate or propionate and the aliphatic carboxylic acid in the composition may be combined together in various ways. For instance, if the aliphatic carboxylic acid is a solid, this can be intimately mixed with the calcium propionate and form a solid mixture. However, if the aliphatic carboxylic is a liquid, this liquid can be used to impregnate the solid calcium acetate or propionate. The admixed or impregnated calcium acetate or propionate can then be stored and used as desired.

The amount of aliphatic carboxylic acid present in the composition along with the respective alkali(ne earth) metal acetate or propionate salt is limited only by the physical ability of the two to be admixed or for the former to be impregnated on the latter. The acetate or propionate salt may, for instance, be admixed or impregnated with 1 to 90% w/w, preferably 40–60% w/w of the aliphatic carboxylic acid based on the total weight of the alkali(ne earth) metal acetate or propionate. An equimolar mixture of the aliphatic carboxylic acid and the acetate or propionate salt is most preferred.

Each of the alkali(ne earth) metal acetate or propionate and the aliphatic carboxylic acid admixed therewith may be, if not a liquid, in the form of a powder or granules or can be shaped into any other convenient shape or form e.g. pellets. The physical shape of the two will be determined by the desired speed of release of the desired acetic or propionic acid once in contact with the appropriate solvent system. It would be clear that for a slow release system, the admixture of the two will be highly compacted.

Whichever form of the components is used in the compositions it will be clear that in order for the acetic acid or propionic acid to be released from the salt, the admixture has to be brought into contact with an aqueous or non-aqueous system, e.g. water, which is capable of allowing the salt and the carboxylic acid to dissociate in said system. Upon intimately mixing the alkali(ne earth) metal acetate or propionate and the aliphatic carboxylic acid with the solvent system, the exchange of ions takes place.

Thus according to a further embodiment, the present invention is a method of releasing free acetic acid or propionic acid in situ in a solvent system capable of allowing the respective acetate or propionate salt of an alkali(ne earth) metal and an aliphatic carboxylic acid having a lower pKa value than that of acetic acid or propionic acid respectively to ionise in said system, said method comprising bringing into contact with the solvent system a composition comprising said acetate or propionate salt and said aliphatic carboxylic acid, thereby generating a solution comprising free acetic or propionic acid respectively in said solvent system.

The following Examples will, for the sake of convenience, be directed to the impregnation of calcium acetate or propionate with fumaric acid but should in no way be construed as limiting the inventive concept disclosed herein.

EXAMPLE 1

1,5 g of 63:67 (w:w) mixture of calcium propionate and fumaric acid were mixed, The mixture was suspended in 100 ml demineralised water in a beaker. After 1 or 2 hours of stirring the sample was transferred to a 250 ml volumetric flask and water was added to 250 ml. After homogenisation, the solution was filtered over a 0.2 microns filter. The propionic acid content in the filtrate was determined by gas chromatography, in five-fold. Quantitative measurements were carried out by external standardisation, i.e. by comparison of the peak area of the sample with that of a propionic acid standard solution of 4 mg/ml. The quantity of propionic acid formed was calculated as follows:

$$\text{mg propionic acid found} = \frac{\text{peak area sample}}{\text{peak area standard}} \times C_{st} \times v_m$$

where $C_{st}$ = concentration of the standard (4 mg/ml)
$V_m$ = volume of the flask (250 ml)

The experiment was carried out on 3 different samples of calcium propionate, A, B and C, each in two-fold.

The maximal concentration of propionic acid that can be obtained is calculated as follows:

mg propionic acid max = intake (mg) $\times P_{cp+} \times C_v \times P_{prop} \times C_c$ in which intake = mg sample $P_{cp}$ = % calcium propionate in the sample/100 (=0.63)

$C_v$ = correction factor for water content of the sample (=0.95)

$P_{prop}$ = % propionate in calcium propionate/100 (=0.784)

$C_c$ = correction factor for the conversion of propionate to propionic acid (=1.013)

$$\text{The yield of the reaction} = \frac{\text{mg propionic acid found}}{\text{mg propionic acid max.}}$$

The results are given in Table 1.

TABLE I

| Sample | | Intake | peak area (10³) | propionic acid found | propionic acid max. | yield (%) |
|---|---|---|---|---|---|---|
| standard 4 mg/ml | | | 546.5 | | | |
| A 1hr stirring | 1 | 1561.3 | 402.5 | 736 | 742 | 99.2 |
| | 2 | 1711.1 | 437.5 | 801 | 813 | 98.5 |
| standard 4 mg/ml | | | 561.5 | | | |
| A 2hr stirring | 1 | 1565.2 | 403.3 | 718 | 744 | 96.5 |
| | 2 | 1680.1 | 449.2 | 800 | 799 | 100.1 |
| standard 4 mg/ml | | | 535.7 | | | |
| B | 1 | 1519.3 | 313.6 | 585 | 722 | 81.1 |
| | 2 | 1772.2 | 344.7 | 644 | 842 | 76.4 |
| standard 4 mg/ml | | | 535.7 | | | |
| C | 1 | 1444.2 | 368.9 | 689 | 687 | 100.3 |
| | 2 | 1458.7 | 383.9 | 717 | 693 | 103.4 |

EXAMPLE 2

1.5g of 58:42 (w:w) mixture of calcium acetate and fumaric acid were mixed. The mixture was suspended in 100 ml demineralised water in a beaker. After 1 hour of stirring the sample was transferred to a 250 ml volumetric flask and water was added to 250 ml. After homogenisation, the solution was filtered over a 0.2 microns filter. The acetic acid content in the filtrate was determined by gas chromatography, in five-fold. Quantitative measurements were carried out by external standardisation, i.e. by comparison of the peak area of the sample with that of an acetic acid standard solution of 4 mg/ml. The quantity of acetic acid formed was calculated as follows:

$$\text{mg acetic acid found} = \frac{\text{peak area sample}}{\text{peak area standard}} \times C_{st} \times v_m$$

where $C_{st}$ = concentration of the standard (4 mg/ml)
$V_m$ = volume of the flask (250 ml)

The experiment was carried out on 3 different samples of calcium propionate, A, B and C, each in two fold.

The maximal concentration of acetic acid that can be obtained is calculated as follows:

mg acetic acid max = intake (mg) $\times P_{ca} \times C_v \times P_{acet} \times C_c$ in which intake = mg sample $P_{ca}$ = % calcium acetate in the sample/100 (=0.573)

$C_v$ = correction factor for water content of the sample (=0.945)

$P_{acet}$ = % acetate in calcium acetate/100 (=0.746)

$C_c$ = correction factor for the conversion of acetate to acetic acid (=1.010)

$$\text{The yield of the reaction} = \frac{\text{mg acetic acid found}}{\text{mg acetic acid max.}}$$

The results are given in Table 2 below.

TABLE 2

| Sample | | Intake | peak area (10³) | acetic acid found | acetic acid max. | yield (%) |
|---|---|---|---|---|---|---|
| standard 4 mg/ml | | | 321.4 | | | |
| A | 1 | 1640.3 | 229.5 | 671 | 714 | 94.0 |
| | 2 | 1507.6 | 198.9 | 618 | 619 | 99.8 |

I claim:

1. A composition consisting essentially of an acetate or a propionate salt of an alkaline earth metal and an aliphatic carboxylic acid which has a lower pKa value than that of the acetic acid or propionic acid, respectively, said aliphatic carboxylic acid being present in the composition with respect to the alkaline earth metal salt of acetic or propionic acid in the range from 1 to 90% by weight.

2. A composition according to claim 1 wherein said composition comprises:
   (a) an alkaline earth metal salt of acetic acid or propionic acid,
   (b) an aliphatic carboxylic acid having a pKa value lower than that of acetic acid or propionic acid, respectively, and
   (c) a solvent system capable of allowing ionisation of the alkaline earth metal salt and the aliphatic carboxylic acid such that when components (a), (b) and (c) are brought together, free acetic acid or propionic acid, respectively, is released into the solvent system in which the alkaline earth metal salt of said aliphatic carboxylic acid is insoluble.

3. A composition according to claim 1 wherein the alkaline earth metal salt is that of calcium or magnesium.

4. A composition according to claim 1 wherein the aliphatic carboxylic acid having a pKa lower than acetic acid or propionic acid, respectively, is a saturated or unsaturated, mono-, di- or polycarboxylic acid.

5. A composition according to claim 1 wherein the aliphatic carboxylic acid having a pKa value lower than that of acetic or propionic acid is selected from the group consisting of transfumaric acid, furoic acid, furan carboxylic acid, lactic acid, maleic acid, malic acid, oxalic acid, malonic acid, succinic acid, methylmalonic acid, methyl succinic acid, gallic acid, m-tartaric acid and mesotartaric acid.

6. A composition according to claim 1 wherein each of the alkaline earth metal salt of acetic or propionic acid and the aliphatic carboxylic acid having a lower pKa value than acetic or propionic acid, respectively, is in a form which is the same or different and is selected from liquid, solution, powder, granules or shaped pellets.

7. A composition according to any one of the preceding claims wherein the alkaline earth metal salt and the aliphatic carboxylic acid are impregnated on a support.

* * * * *

UNITED STATES PATENT AND TRADEMARK OFFICE
CERTIFICATE OF CORRECTION

PATENT NO. : 5,380,939
DATED : January 10, 1995
INVENTOR(S) : JOHANNES A.C. VAN OOIJEN It is certified that error appears in the above-indentified patent and that said Letters Patent is hereby corrected as shown below:

Col. 3, line 12, "compositions" should read —composition—.
Col. 3, l. 12, insert a comma (,) after "composition"

Col. 3, l. 40, should read "1.5g"
Col. 6,
Claim 5, line 17, change "m-tartaric" to —$\alpha$-tartaric"

Signed and Sealed this

Twenty-fifth Day of April, 1995

Attest:

BRUCE LEHMAN

Attesting Officer   Commissioner of Patents and Trademarks